United States Patent [19]

De Jong

[11] 4,116,795

[45] Sep. 26, 1978

[54] SENSOR DEVICE

[75] Inventor: Herman Lambertus De Jong, Eindhoven, Netherlands

[73] Assignee: U.S. Philips Corporation, New York, N.Y.

[21] Appl. No.: 792,648

[22] Filed: May 2, 1977

[30] Foreign Application Priority Data

May 12, 1976 [NL] Netherlands .......................... 7605042

[51] Int. Cl.² ............................................ G01N 27/46
[52] U.S. Cl. .............................. 204/195 S; 123/119 E
[58] Field of Search .............................. 204/15, 195 S; 123/119 E

[56] References Cited

U.S. PATENT DOCUMENTS

| | | | |
|---|---|---|---|
| 3,835,012 | 9/1974 | Hemak | 204/195 S |
| 3,928,161 | 12/1975 | McIntyre et al. | 204/195 S |
| 4,040,930 | 8/1977 | Dillon | 204/195 S |

FOREIGN PATENT DOCUMENTS 2,348,505  3/1975  Fed. Rep. of Germany ....... 204/195 S

*Primary Examiner*—T. Tung
*Attorney, Agent, or Firm*—Frank R. Trifari

[57] ABSTRACT

Sensor for measuring the oxygen concentration in the exhaust gases of combustion engines, in which zirconium oxide is used as active material. The improvement relates to a composite filter so that the response is great and the contamination at the same time low. For practical applications the life is consequently attractive.

1 Claim, 1 Drawing Figure

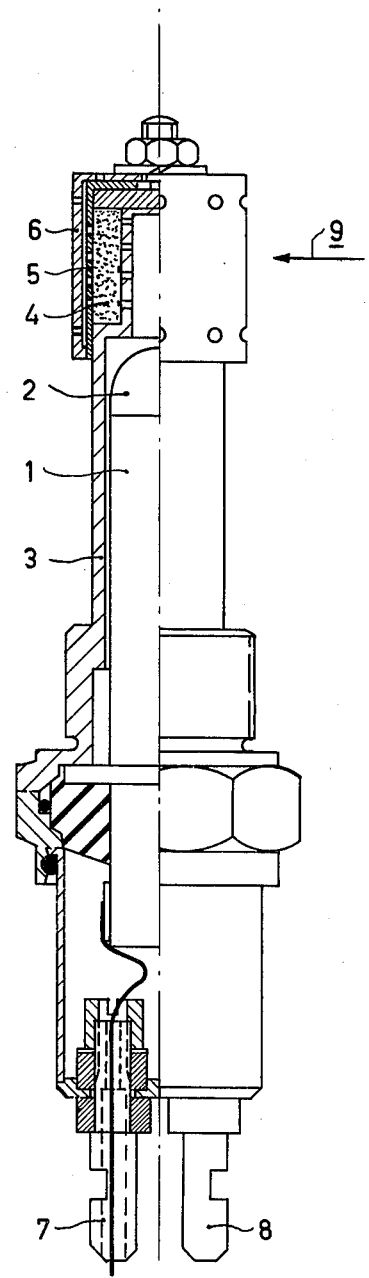

SENSOR DEVICE

The invention relates to a sensor device for measuring the oxygen concentration in exhaust gases of combustion engines.

Such a device which consists of the sensor proper and a filter for preventing the sensor from becoming inoperable due to contamination is disclosed in U.K. Patent specification 1,407,928 and corresponding U.S. Pat. No. 3,819,500.

The sensor for measuring oxygen concentrations is used for measuring the concentration of the carbon monoxide in the exhaust gas, as, at low concentrations, this carbon monoxide being in equilibrium with oxygen in accordance with the equation $$CO + \tfrac{1}{2}O_2 \rightleftarrows CO_2.$$

The sensor is, for example, known from the "Journal Electrochemical Society" 109, 723-726 (1962). It has a partition consisting of a solid material undergoing a reversible reaction with oxygen and exhibiting ionic conductivity, which partition is provided on both sides with a thin metallic electrode layer. According to the embodiment to which the relevant invention relates, such a solid material of the partition is zirconium oxide stabilized by CaO or $Y_2O_3$, which exhibits conductivity by means of oxygen ions while the electrodes consist of a noble metal, platinum in particular. The gas mixture whose partial oxygen pressure must be measured is present on one side of the partition. The outer air which functions as a reference gas having a constant partial oxygen pressure is present on the other side. At the temperature of the exhaust system during operation, (that is to say, between approximately 400° and 850° C) a voltage difference, E, is produced by movement of the ions between the two sensor electrodes, which difference, in accordance with the Nernst equation $$E = \frac{RT}{2zF} \ln \frac{p_1}{p_2}$$

depends on the ratio of the partial pressures $p_1$ and $p_2$.

In this equation R is the gas constant in Joules /° C, T is the absolute temperature, z is the valency of the oxygen ions and F the Faraday constant in Coulombs.

The exhaust gases of a combustion engine may contain an excess of oxygen in the combustion of poor fuel air-mixtures. When rich mixtures are combusted the exhaust gas will contain an excess of carbon monoxide which, at the platinum-surface of a sensor device reacts with oxygen which is present there in atomic form. Then the partial oxygen pressure at that side of the sensor becomes very low and the difference in partial pressure on either side of the $ZrO_2$ wall becomes very large. The transition from a poor to a rich mixture is therefore characterized by a large voltage shift of approximately 500 mV. This large voltage difference is used for controlling this magnitude in a member for controlling the air-fuel-ratio.

When placing the sensor device in the exhaust gas stream, the electrodes in particular are exposed to heavy wear by the collision of coarse particles from the combustion gases.

In addition, after having been exposed for a comparatively short period of time to the action of exhaust gases a deposit is formed on the electrodes, which shield the surface of the electrodes and greatly inhibits the catalytical operation thereof. The result thereof is that both the sensitivity of the sensor and its response strongly decrease.

Especially the lead compounds present in the petrol, which, after combustion, result in fine lead oxide particles or particles of metallic lead, are very detrimental to the proper operation of the Pt electrodes as a catalysor and considerably shorten the life of the sensor.

In order to mitigate said disadvantages the above-mentioned patent application proposes to equip the sensor with a filter. As a customary filter, for example consisting of sintered stainless steel, clogs comparatively rapidly and, consequently, blocks the contact of the measuring gas with the sensor recourse was had to a so-called diffusion filter. Such a filter is placed in such a manner that the measuring gas flows along it and consequently blows directly against it.

Applicants ascertained that this indeed strongly reduces the contamination but that it resulted in an extremely slow response, so that, when the sensor is placed in the exhaust of a combustion engine a far-too-slow reaction to changes in the composition of the exhaust gas occurs.

It is an object of the invention to provide a sensor device wherein the sensor is provided with a filter which offers sufficient protection against contamination of the sensor and which also guarantees a rapid response.

The sensor device according to the invention is characterized in that the filter which is located between the sensor element of the device and the source of the exhaust gas consists of a combination of three or more partition walls provided with apertures, which apertures have a diameter which by far exceeds the average diameter of the particles to be filtered and which, at least in the two outermost partitions, are not in register, the partitions being mutually separated by a space, so that owing to this combination the gas stream changes direction and coarser particles are separated from the gas stream, and that at the same time a fine-mesh, sintered or fibrous filter material is present between two partitions at the side of the sensor.

The apertures in the partions are preferably in the order of magnitude of 1 mm. The fine-mesh filtering material may consist essential of, e. g., sintered nickel powder, sintered stainless steel powder, coarse porous ceramic, quartz glass fibres, alundum fibres etc.

The invention will now be further explained with reference to a drawing, which depicts in partial sectional view the present invention.

In this drawing which is drawn to a scale 2 : 1 (linear), the sensor 1 consists of a body of stabilized $ZrO_2$, with a vapor-deposited platinum coating 2 providing the outer electrode. Not shown is another similar platinum coating at the inner side which acts as the other electrode. These electrode layers are electrically interconnected to the contact pins 7 and 8 and the sensor is enveloped by an envelope 3 which has a smaller diameter at the top and which is provided with apertures. Between this component and the cover 5 which is also provided with apertures, fibrous quartz glass or alundum 4 is present, packed between fine chromium nickel steel gauze. Disposed around the cover 5 there is a distributor cap 6, which is also provided with apertures, which leaves an open space around the cover 5. The apertures in the distributor cap 6 and those in the filter bush or cover 5 are not in register. The gas stream 9 which impinges on the distributor cap enters through the apertures and follows its way through the apertures in the bush 5. The stream makes a detour, which causes the coarser particles to stay behind in the space between cover 5 and distributor cap 6.

After having been used in a combustion engine vehicle for 25 kms the sensor without the filter is covered with a dense deposit and has then become less sensitive already. In the sensor device according to the invention the sensor is not visibly contaminated even after 10,000 kms (magnification 10,000 x in the scanning electron microscope). Response and sensitivity have then hardly decreased. Super petrol doped with tetra ethyl lead was used in these tests.

What is claimed is:

1. A sensor device for measuring the oxygen concentration in the exhaust gases of combustion engines wherein said gases include particles that are to be filtered, comprising a sensor element that comprises a body element of stabilized $ZrO_2$ having electrode layers on both sides, said device further comprising a filter member that comprises a combination of at least three apertured partitions, a first one of said partitions being disposed between a second partition and a third partition and said partitions being spaced from each other, said partition apertures having diameters which significantly exceed the average diameter of the particles to be filtered and not being in register at least in the two outermost said partitions, so that this combination of apertures changes the direction of the gas stream and coarser said particles are separated from the gas stream; and further comprising a filter element that is a fine-meshed, sintered or fibrous filtering material and is present between two of said partitions located closer to said sensor element than the outermost said partition, said filter member being disposed between said sensor and the source of said exhaust gases.

* * * * *